United States Patent
Akiba et al.

(10) Patent No.: US 8,925,389 B2
(45) Date of Patent: Jan. 6, 2015

(54) METHOD FOR MEASURING STRENGTH OF CHEMICALLY STRENGTHENED GLASS, METHOD FOR REPRODUCING CRACKING OF CHEMICALLY STRENGTHENED GLASS, AND METHOD FOR PRODUCING CHEMICALLY STRENGTHENED GLASS

(75) Inventors: Shusaku Akiba, Tokyo (JP); Takahiro Sakagami, Tokyo (JP); Kazutaka Ono, Tokyo (JP)

(73) Assignee: Asahi Glass Company, Limited, Tokyo (JP)

( * ) Notice: Subject to any disclaimer, the term of this patent is extended or adjusted under 35 U.S.C. 154(b) by 250 days.

(21) Appl. No.: 13/606,510

(22) Filed: Sep. 7, 2012

(65) Prior Publication Data
US 2013/0061635 A1 Mar. 14, 2013

(30) Foreign Application Priority Data
Sep. 13, 2011 (JP) .................. 2011-199555

(51) Int. Cl.
*G01N 3/00* (2006.01)
*G01N 3/42* (2006.01)
*G01N 3/40* (2006.01)

(52) U.S. Cl.
CPC ... *G01N 3/42* (2013.01); *G01N 3/40* (2013.01)
USPC ................................ 73/788; 73/81

(58) Field of Classification Search
CPC ............. G01N 3/42; G01N 3/40; G01N 3/08; G08B 13/04
USPC ............................. 73/81, 788, 821
See application file for complete search history.

(56) References Cited

U.S. PATENT DOCUMENTS

| | | | | |
|---|---|---|---|---|
| 4,857,119 | A * | 8/1989 | Karst et al. ................... | 148/219 |
| 5,602,329 | A * | 2/1997 | Haubensak ...................... | 73/82 |
| 6,142,010 | A * | 11/2000 | Merck et al. ..................... | 73/81 |
| 8,215,223 | B2 * | 7/2012 | Lucuta et al. ................ | 89/36.02 |
| 2003/0141974 | A1 * | 7/2003 | Allen ......................... | 340/545.1 |
| 2007/0068605 | A1 * | 3/2007 | Statnikov ..................... | 148/558 |
| 2009/0202808 | A1 * | 8/2009 | Glaesemann et al. ......... | 428/220 |
| 2014/0036644 | A1 * | 2/2014 | Matsumoto et al. ....... | 369/13.24 |

FOREIGN PATENT DOCUMENTS

| | | |
|---|---|---|
| JP | 2010-243387 A | 10/2010 |
| JP | 2011-510903 A | 4/2011 |
| JP | 2011-105598 | 6/2011 |
| WO | WO 2011/145661 A1 | 11/2011 |

* cited by examiner

*Primary Examiner* — Max Noori
(74) *Attorney, Agent, or Firm* — Oblon, Spivak, McClelland, Maier & Neustadt, L.L.P.

(57) ABSTRACT

There are provided a method for measuring strength of a chemically strengthened glass, that reflects the state of actual drop fracture more appropriately, and can reproduce slow cracking in the chemically strengthened glass, a method for reproducing cracking of a chemically strengthened glass, and a method for producing a chemically strengthened glass. Load is applied to an indenter having a tip formed into a sharp shape having a minimum angle θmin of cross-section of less than 120°, the indenter is pushed into a chemically strengthened glass under a static load condition such that the tip is vertical to a surface of the chemically strengthened glass, and the load when the chemically strengthened glass cracks is measured.

17 Claims, 13 Drawing Sheets

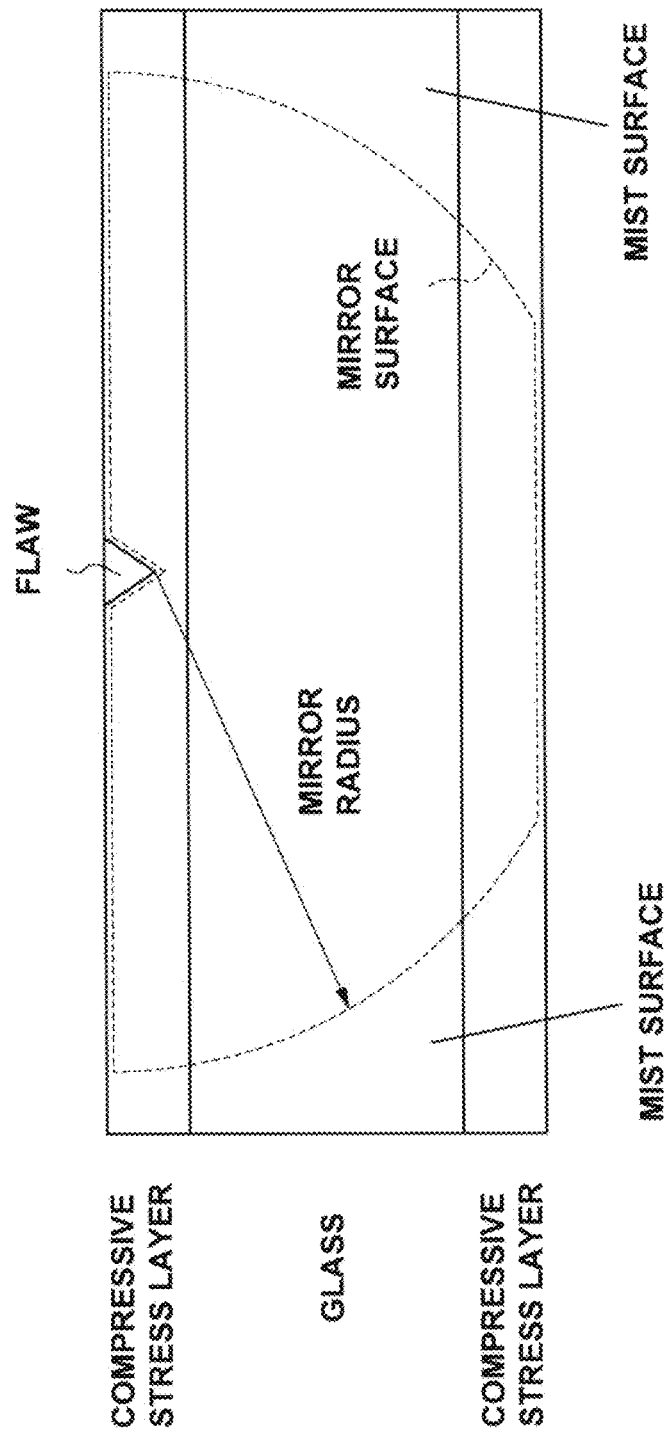

FIG.11

GLASS: A

| MINIMUM ANGLE θmin OF CROSS-SECTION | LOAD (kgf) 0.05 | 0.5 | 1 | 3 |
|---|---|---|---|---|
| 136° (VICKERS INDENTER) | ×40 | ×40 | ×40 | ×40 |
| 110° | ×40 | ×40 | ×10 | ×10 |
| 60° | ×40 | ×5 | | |

METHOD FOR MEASURING STRENGTH OF CHEMICALLY STRENGTHENED GLASS, METHOD FOR REPRODUCING CRACKING OF CHEMICALLY STRENGTHENED GLASS, AND METHOD FOR PRODUCING CHEMICALLY STRENGTHENED GLASS

FIELD OF THE INVENTION

The present invention relates to a method for measuring strength of a chemically strengthened glass having formed thereon a compressive stress layer by chemically strengthening, a method for reproducing cracking of a chemically strengthened glass, and a method for producing a chemically strengthened glass.

BACKGROUND OF THE INVENTION

Recently, to increase protection and beauty of a display in flat panel display devices such as mobile phones and personal digital assistances (PDA), a thin plate-shaped cover glass is provided on a front surface of a display so as to form a region wider than an image display portion. Weight reduction and thickness reduction are required to such flat panel display devices, and to achieve those requirements, a cover glass used for protecting a display is also required to reduce its thickness. However, where the thickness of the cover glass is reduced, strength is decreased, and the cover glass itself may crack by dropping during the use or during carrying. Thus, there has been a problem that the primary function of protecting a display device cannot be performed.

For this reason, a conventional cover glass has increased its strength by chemically strengthening a glass plate to form a compressive stress layer on the surface thereof (for example, JP-A-2011-105598).

Since a flat panel display device is portable, it is considered that, among cases where a cover glass has fractured, there are a lot of cases where a stone or the like collides with a glass surface by dropping the device, and the cover glass fractures starting from a crack generated by the indentation. That is, high resistance to indentation, rather than bending strength, is required as strength of a cover glass.

Conventionally, to evaluate strength of such a cover glass, superiority or inferiority of a cover glass has been evaluated by pushing an indenter having relatively large tip angle, such as Vickers indenter or Knoop indenter, into a surface of a cover glass and comparing easiness of occurrence of cracks occurred from the indentation. However, there is a case where superiority or inferiority of the cover glass evaluated by the above-mentioned method does not always correlate with superiority or inferiority of the cover glass in the actual drop fracture, and a measurement method for strength of a glass further appropriately reflecting the situation of the actual drop fracture has been demanded. Furthermore, there has been a problem that fracture pattern of a glass in the above-mentioned method does not always consist with the actual drop fracture pattern.

In actually giving impact to a cover glass in, for example, the case that users drop a flat panel display device by mistake, slow crack in which a glass cracks in relatively slow rate starting from a flaw penetrating a compressive stress layer may occur even in a chemically strengthened cover glass (such cracking manner of a glass is hereinafter referred to as "slow cracking").

Such a slow cracking occurs under lower load or by drop from lower place, as compared with so-called edge cracking or spider cracking described hereinafter, and the slow cracking remarkably differs from the cracking conventionally been problematic, in terms of this point.

In the study to the slow cracking and the development of a cover glass resistant to the slow cracking, that have hitherto been made, it has been extremely difficult to reproduce the slow cracking. For example, it has been difficult to cause the slow cracking by pushing an indenter having relatively large tip angle, such as Vickers indenter, into a glass. For this reason, it was necessary that a considerable number of fabricated flat panel display devices are fractured by dropping them on the ground or the like, glasses accidentally causing slow cracking are then extracted from the cracked glasses and those glass are evaluated.

However, reproduction of slow cracking by dropping a flat panel display device that is an actual product on the ground leads to not only poor efficiency, but the waste of the flat panel display device itself. For this reason, it has been desired to reproduce slow cracking in a chemically strengthened glass at the stage before a flat panel display device becomes a product.

SUMMARY OF THE INVENTION

The present invention has been made in view of the above problems, and an object thereof is to provide a method for measuring strength of a chemically strengthened glass, that reflects the state of the actual drop fracture more appropriately and can reproduce slow cracking in a chemically strengthened glass, a method for reproducing cracking of a chemically strengthened glass, and a method for producing a chemically strengthened glass.

The present invention provides the following items.

1. A method for measuring strength of a chemically strengthened glass, comprising:

applying a load to an indenter having a tip formed into a sharp shape having a minimum angle of cross-section of less than 120°, pushing the indenter into a chemically strengthened glass having a compressive stress layer formed on a surface thereof under a static load condition such that the tip is vertical to the surface of the chemically strengthened glass, and measuring the load when the chemically strengthened glass cracks.

2. The method for measuring strength of a chemically strengthened glass according to item 1 above, wherein the minimum angle of cross-section of the tip is 30° or more.

3. A method for reproducing cracking of a chemically strengthened glass, comprising applying a static load to a chemically strengthened glass having a compressive stress layer formed on a surface thereof to form a flaw deeper than a thickness of the compressive stress layer.

4. The method for reproducing cracking of a chemically strengthened glass according to item 3 above, comprising applying a load to an indenter having a tip formed into a sharp shape having a minimum angle of cross-section of less than 120°, and pushing the indenter into the chemically strengthened glass under a static load condition such that the tip is vertical to the surface of the chemically strengthened glass.

5. The method for reproducing cracking of a chemically strengthened glass according to item 4 above, wherein the minimum angle of cross-section of the tip is 30° or more.

6. A method for producing a chemically strengthened glass having a compressive stress layer formed on the surface thereof, comprising:

determining a threshold by the method for measuring strength of a chemically strengthened glass according to item 1 above while changing a load by an indenter, and conducting a sampling inspection for judging quality of the chemically strengthened glass on the basis of the threshold.

7. The method for producing a chemically strengthened glass according to item 6 above, wherein the minimum angle of cross-section of the tip is 30° or more.

According to the method for measuring strength of a chemically strengthened glass described in item 1 above, strength can be measured in a state approximate to collision to the ground or the like when a glass has actually dropped, by applying a load to an indenter having a tip formed into a sharp shape having a minimum angle of cross-section of less than 120°, pushing the indenter into a chemically strengthened glass under a static load condition such that the tip is vertical to the surface of the chemically strengthened glass, and measuring the load when the chemically strengthened glass cracks. This makes it possible to further appropriately reflect the state of the actual drop fracture.

According to the method for measuring strength of a chemically strengthened glass described in item 2 above, the minimum angle of cross-section of the tip of the indenter is 30° or more, and this makes it possible to further appropriately reflect the state of the actual drop fracture.

According to the method for reproducing cracking of a chemically strengthened glass described in item 3 above, slow cracking occurred in a flat panel display device can be reproduced, and even though a flat panel display device itself is not actually dropped, slow cracking can be generated by using only a chemically strengthened glass. Therefore, the method can be utilized to development of new glass material, and the like.

According to the method for reproducing cracking of a chemically strengthened glass described in item 4 or item 5 above, a state near a state where a flat panel display device has actually dropped on the ground can be created, and reproducibility of slow cracking can be improved.

According to the method for producing a chemically strengthened glass described in item 6 above, cracking performance of a chemically strengthened glass can be controlled further accurately while further appropriately reflecting the state where a flat panel display device has actually dropped.

BRIEF DESCRIPTION OF THE DRAWINGS

FIGS. 2A and 2B are views schematically showing mechanism that slow cracking occurs, in which FIG. 2A is a view showing a fracture origin, and FIG. 2B is a view showing a crack.

FIG. 6 is a view schematically showing the fracture surface of FIG. 5.

FIGS. 10A and 10B are views schematically showing mechanism that cracking of a chemically strengthened glass occurs in the method for reproducing slow cracking shown in FIG. 8, in which FIG. 10A is a graph showing a fracture origin, and FIG. 10B is a view showing a crack.

FIG. 11 shows photographs of the chemically strengthened glass in Example 1.

DESCRIPTION OF REFERENCE NUMERALS AND SIGNS

Figure 1:
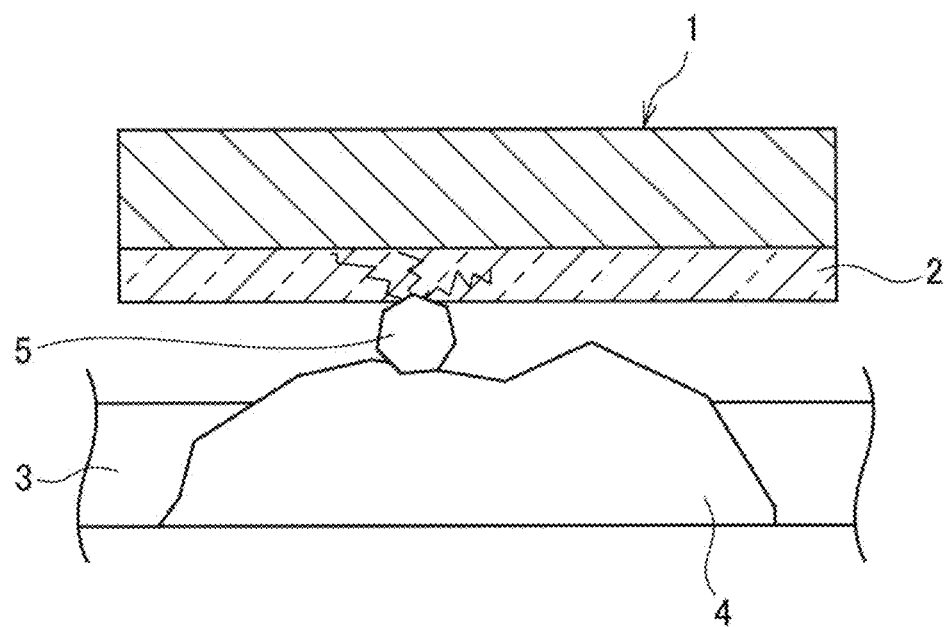
FIG. 1 is a schematic view showing a state that slow cracking occurs in a cover glass when a flat panel display device actually dropped.

1 Flat panel display device
2 Cover glass
3 Asphalt/concrete
4 Small stone
5 Sand
10 Chemically strengthened glass
10a Upper Surface
10b Lower surface
11 Vickers hardness tester
12 Board
16 Indenter
16a Tip
16b Bottom surface
O Fracture origin
θ Angle of cross-section
θmin Minimum angle of cross-section

DETAILED DESCRIPTION OF THE INVENTION

The method for measuring strength of a chemically strengthened glass and the method for reproducing cracking of a chemically strengthened glass, according to the present invention are described below. Mechanism of slow cracking occurred when a flat panel display device dropped is first described.

Figure 2A:
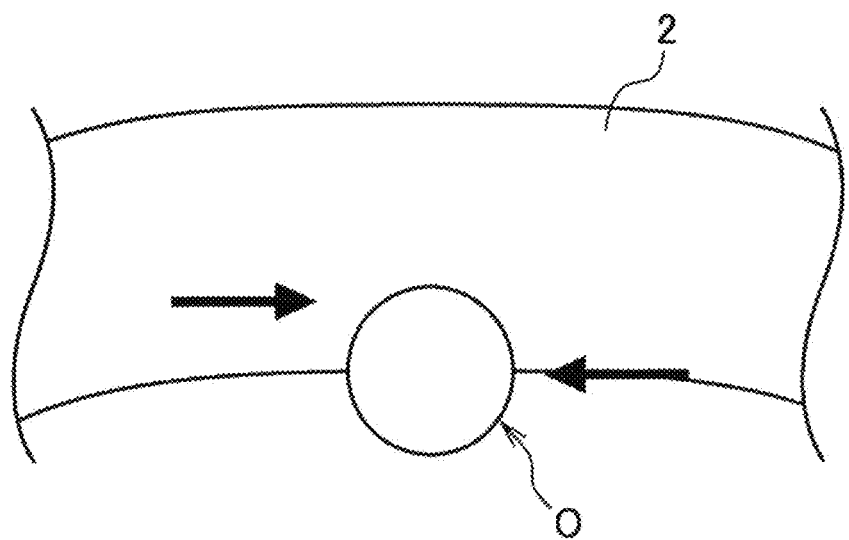
Figure 2B:
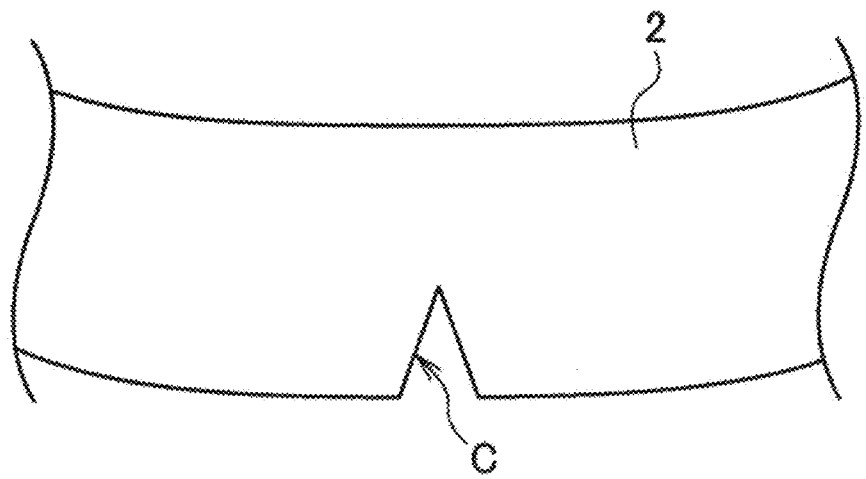
Figure 3A:
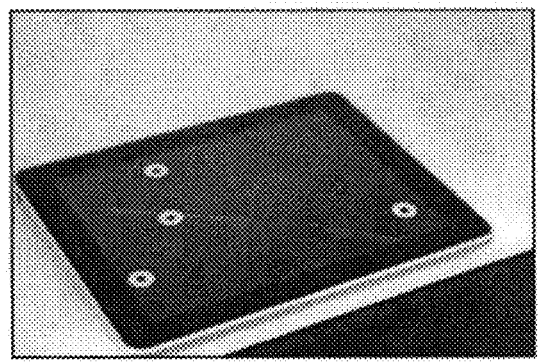
FIG. 3A is a view showing a photograph of a flat panel display device in which slow cracking occurred.
Figure 3B:
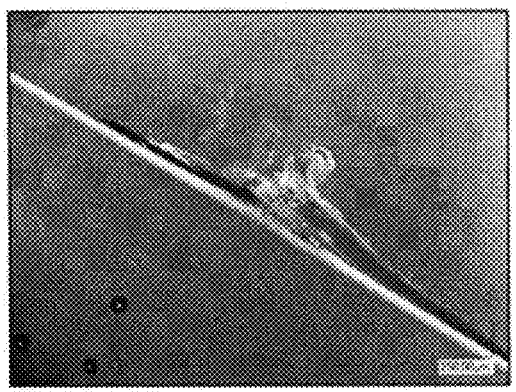
FIG. 3B is a view showing an enlarged photograph seeing a fracture origin from an upper part.
Figure 3C:
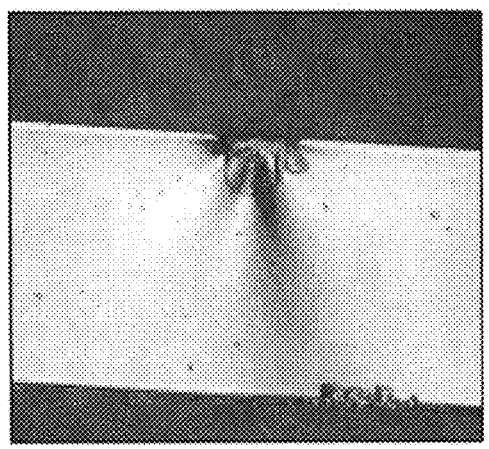
FIG. 3C is a view showing a photograph seeing a fracture origin from a side.

FIG. 1 is a schematic view showing the state that a slow cracking occurs in a cover glass 2 when a flat panel display device 1 dropped, FIGS. 2A and 2B are views schematically showing mechanism that a slow cracking occurs, FIG. 3A is a view showing a photograph of a flat panel display device in which a slow cracking occurred, FIG. 3B is a view showing an enlarged photograph seeing a fracture origin from an upper part, and FIG. 3C is a view showing a photograph seeing a fracture origin from a side.

A flat panel display device includes an image display, a nearly rectangular frame provided so as to surround the image display, and a cover glass supported on the frame. When the flat panel display device 1 drops on the ground (asphalt/concrete) and the cover glass 2 comes into contact with sand 5 and the like on a small stone 4 in asphalt/concrete 3 in the state that the cover glass 2 faces down, as shown in FIG. 1, compressive stress acts to a fracture origin O, and tensile stress acts to the periphery of the point (FIG. 2A). Subsequently, tensile stress acts to the fracture origin O, crack C extends, and the cover glass 2 cracks (FIG. 2B). The fracture origin may occur at a central portion of the cover glass.

However, because deflection of the cover glass is restrained by a frame, the fracture origin frequently occurs in a part of a region supported by the frame.

The cracking of the cover glass 2 in this case is such that a flaw deeper than the depth of the compressive layer becomes the fracture origin, as is apparent from the fracture surface of FIG. 3C. In FIGS. 3A and 3B, one crack extends from the fracture origin, and the cover glass is split in two. Further observing the fracture surface shown in FIG. 3C, a mirror surface that is smooth like a mirror and has long mirror radius is observed around the fracture origin deeper than the depth of the compressive stress layer.

Figure 4:
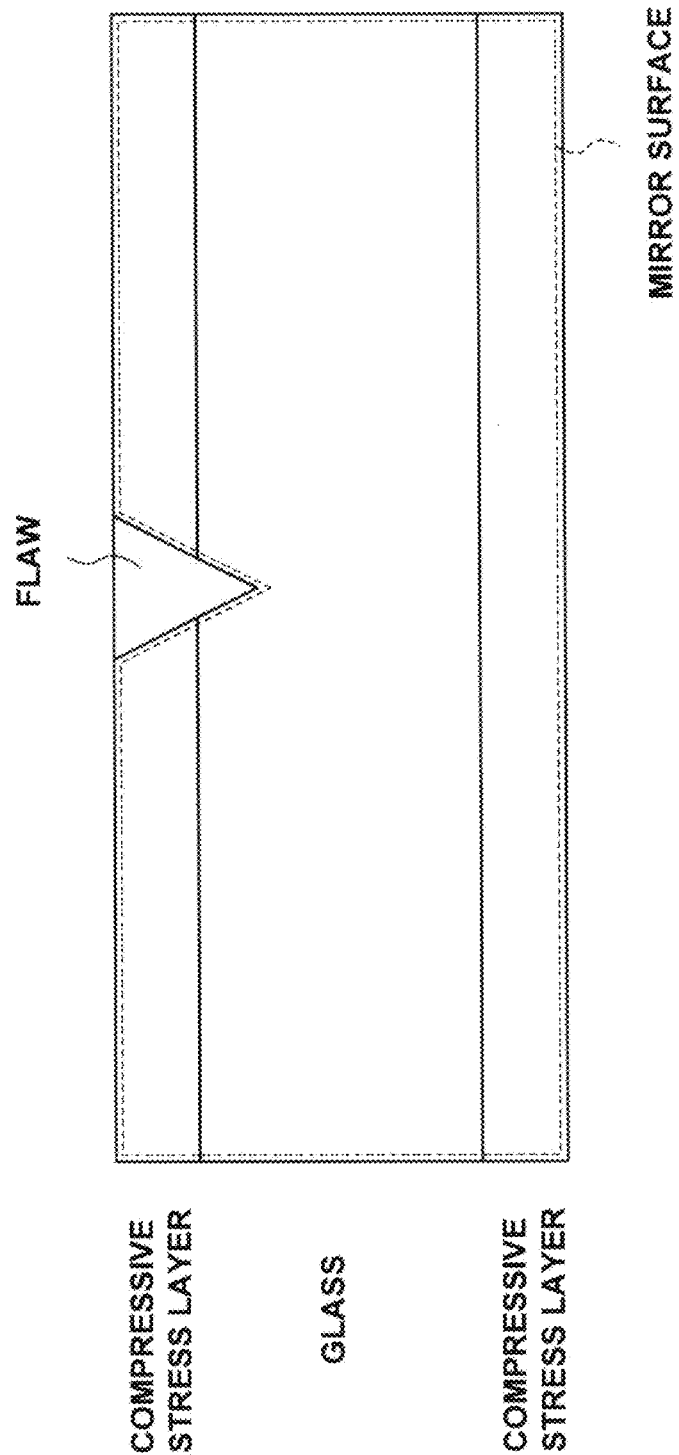
FIG. 4 is a view schematically showing the fracture surface of FIG. 3C.

FIG. 4 is a view schematically showing the fracture surface of FIG. 3C. Processes of fracture, that is, factors such as fracture origin, a traveling direction of the fracture, whether the fracture progresses mildly or proceeds rapidly, and the like, are reflected on the fracture surface. According to the analysis of fracture surface of the slow cracking, a mirror surface having long mirror radius means that fracture progressed by small stress, and the smooth fracture surface means that crack grown in a speed far slower than the speed of sound. Therefore, according to the fracture surface of FIG. 3C, it is seen that after an origin deeper than the depth of the compressive stress layer was formed in a cover glass, crack gradually grew and fracture progressed by small stress. In the cover glass cracked by the slow cracking, the number of broken pieces becomes several pieces to (as the case may be) several ten pieces. Typically, the number is 2 pieces to 20 pieces, and the example in which one crack extended from the fracture origin shown in FIGS. 3A and 3B and a cover glass was split in two is a typical example of the slow cracking.

Whether or not a slow cracking occurs is more microscopically judged as follows. Unless the fracture origin is observed, the cracking is not said to be a slow cracking. Furthermore, in a case that the vicinity of the fracture origin is observed and a flaw penetrating a compressive stress layer, that is, a flaw deeper than the depth of the compressive stress layer (so-called DOL) is confirmed to be the fracture origin, the cracking is a slow cracking. In a case that a mirror surface radius is long, the fracture surface is a mirror surface and mist and hackle are not observed, the cracking is a slow cracking.

As described above, it is very difficult to reproduce a slow cracking, and even if only a cover glass is dropped on the ground, a slow cracking may accidentally occur, but reproducibility is not obtained. That is, a cracking that is not a slow cracking (hereinafter referred to as "non-slow cracking") occurs in many cases, and cover glasses are wasted.

Figure 5:
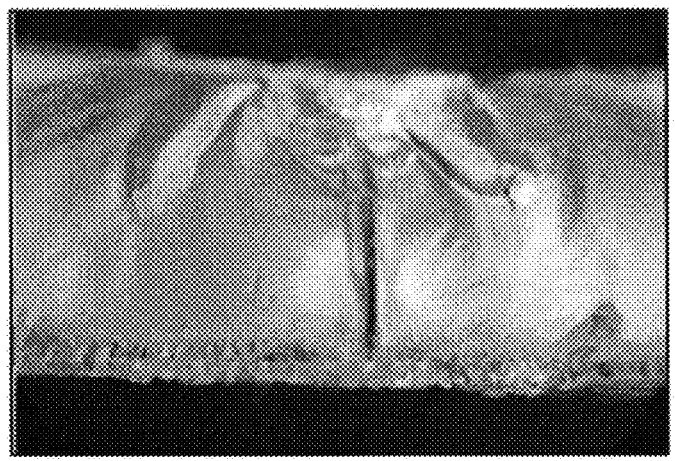
FIG. 5 is a view showing a photograph seeing a fracture origin of a cover glass in which a non-slow cracking occurred, from a side.

A cracking of a cover glass, caused by pushing Knoop indenter into a surface of a glass is described as a non-slow cracking that is compared with a slow cracking. FIG. 5 is a view showing a photograph seeing a fracture origin of a cover glass in which a non-slow cracking occurred, from a side, and FIG. 6 is a view schematically showing the fracture surface of FIG. 5.

Observing the fracture surface of the non-slow cracking, the fracture origin is formed in the compressive stress layer, a mirror surface having a short mirror radius, that is smooth like a mirror is observed around the fracture origin, and mist surface is present around the mirror surface. According to the analysis of fracture surface of the non-slow cracking, the mirror surface having a short mirror radius means that a fracture progressed by large stress, and the mist surface means that the crack rapidly grew. Therefore, according to the fracture surface of FIG. 5, it is seen that after the fracture origin shallower than the depth of the compressive stress layer was formed on the cover glass, the fracture progressed by large stress and the crack rapidly grew. Where the non-slow cracking occurs, a lot of glass pieces (20 pieces or more) are formed by a plurality of cracks extending in a spiderweb shape (this cracking manner is hereinafter called "spider cracking"). Thus, it is seen that the fractures occur in quite different modes between the slow cracking and the non-slow cracking.

Concerning the non-slow cracking, the fracture origin occurs in the compressive stress layer. To prevent this, it is effective to increase the surface compressive stress or increase the depth of the compressive stress layer. However, concerning the slow cracking, the fracture origin occurs in a region exceeding the compressive stress layer (the depth of a flaw is typically several ten to several hundred and the compressive stress layer by chemical strengthening has a thickness of several to several ten μm). Therefore, it is necessary to develop a cover glass having mechanical characteristics that are resistant to slow cracking. For this reason, reproduction of a slow cracking in a chemically strengthened glass used as a cover glass is very important to proceed with future research and development.

Figure 7A:
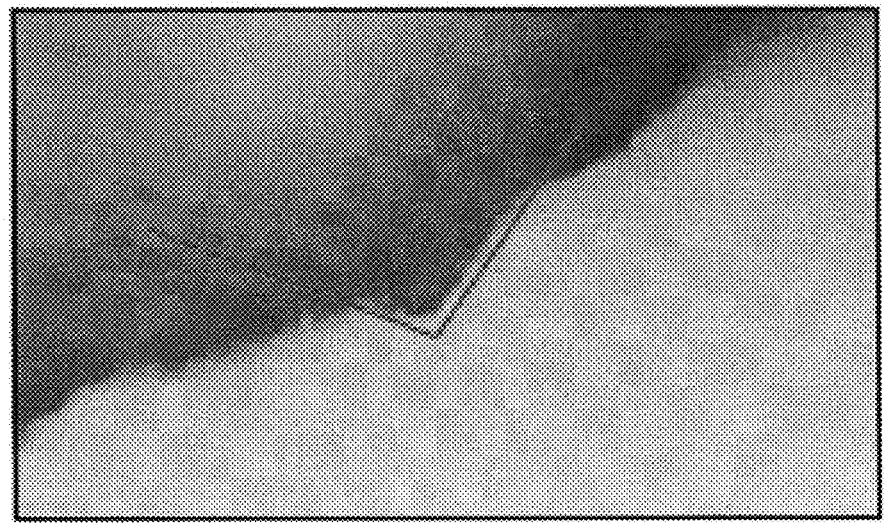
FIG. 7A is a view showing an enlarged photograph of asphalt/concrete.
Figure 7B:
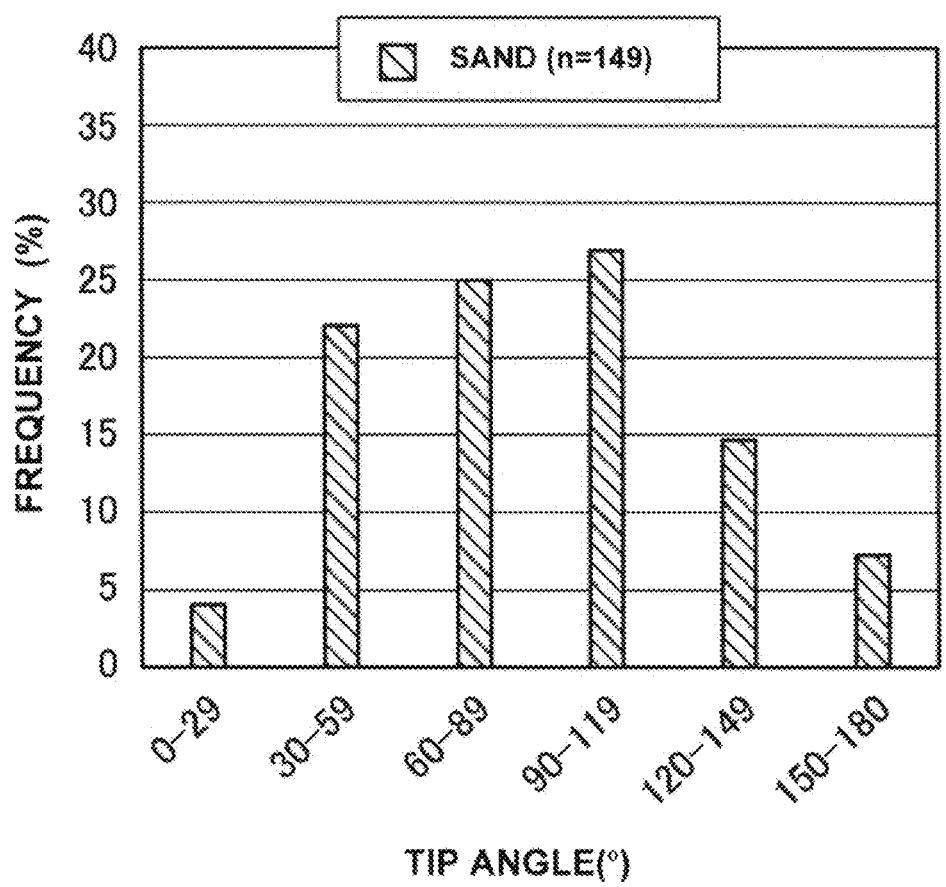
FIG. 7B is a graph showing an angle distribution of tip of sand.

However, in a case that Vickers indenter or Knoop indenter is pushed into a glass surface as described above, a non-slow cracking occurs in a cover glass (see FIG. 5), and a slow cracking cannot be reproduced. FIG. 7A shows an enlarged photograph of sand and small stone contained in asphalt/concrete (collected in Yokohama), and FIG. 7B is a graph in which asphalt/concrete were observed at 149 places, a horizontal axis shows a tip angle of sand and small stone, and a longitudinal axis shows frequency. As shown in FIG. 7B, sand and small stone contained in asphalt/concrete are largely distributed in a range of an angle of 30° or more and less than 120°, and are not largely distributed in a range containing an angle (136°) of the tip of Vickers indenter and an angle (172.3° and 130°) of the tip of Knoop indenter.

From the above fact, the present inventors have found a method for reproducing a slow cracking by making a hypothesis that the reason that the slow cracking cannot be reproduced in the case of using Vickers indenter and Knoop indenter is that an angle of the tip of the conventional indenter is large as compared with an angle of sand and the like contained in asphalt/concrete, and by approaching the angle of the tip of the indenter to an angle distribution of the actual sand and the like.

The slow cracking means that a fracture origin deeper than the depth of the compressive stress layer is formed and cracking occurs, as described above. Typically, a number of the broken pieces are 2 to 20 pieces. On the contrary, the non-slow cracking occurred from the origin in the compressive stress layer forms finely broken glass pieces, and is therefore a quite different mode from the slow cracking.

Embodiments

Figure 8:
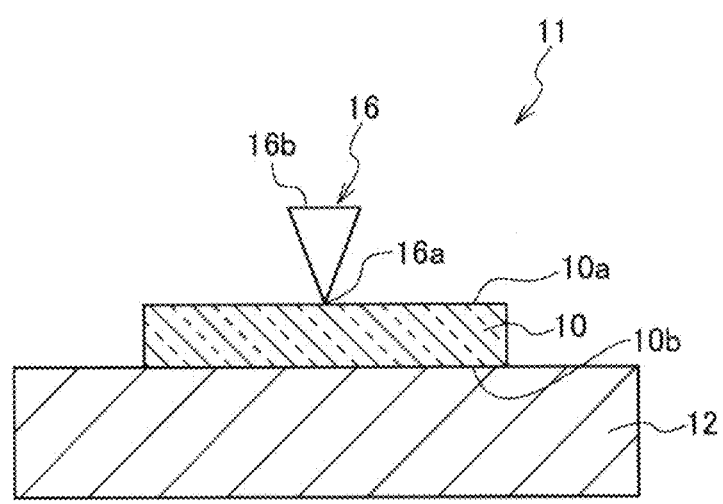
FIG. 8 is a schematic view of a method for reproducing slow cracking according to one embodiment of the present invention.

As shown in FIG. 8, the method for reproducing cracking of a chemically strengthened glass according to one embodiment of the present invention uses a conventional Vickers hardness tester 11, but the method of the present invention is not limited thereto. The tester 11 comprises a board 12 that can mount a chemically strengthened glass 10 thereon, and an indentation mechanism (not shown) that movably holds an indenter 16 placed on an upper part of the board 12. The tester 11 is equipped with a lens (not shown) for the measurement of depression, a sample surface shape detection mechanism (not shown), and the like, similar to the conventional Vickers hardness tester, and is appropriately used to evaluate the surface of the chemically strengthened glass 10.

The chemically strengthened glass 10 has compressive stress layers formed on an upper surface 10a and a lower surface 10b, and is placed on the board 12 such that the upper surface 10a faces up. The chemically strengthened glass 10 is disposed such that the entire surface of the lower surface 10b is in contact with the board 12, and is constituted such that deflection by the weight itself or deflection by a load of the indenter 16 is restrained by the board 12.

The indenter 16 is a right pyramid-shaped diamond indenter, and is arranged such that the tip (vertex) 16a is vertical to the upper surface 10a of the chemically strengthened glass 10.

Figure 9A:
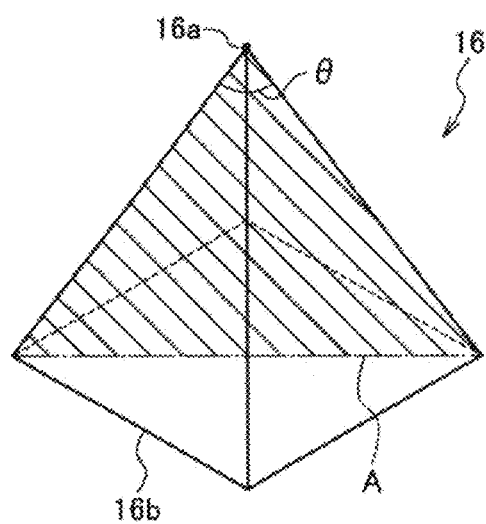
FIGS. 9A and 9B are perspective views of an indenter.
Figure 9B:
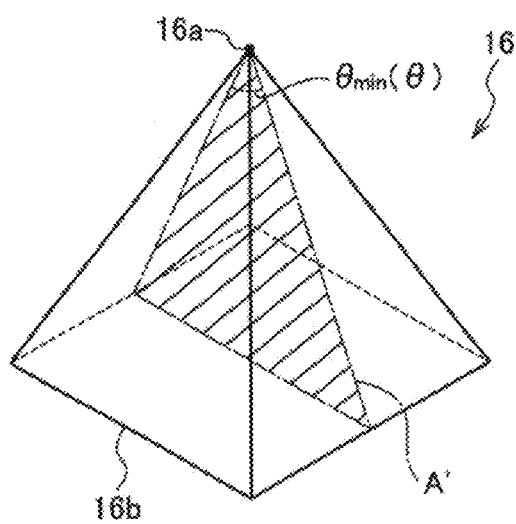

The tip 16a of the indenter 16 is formed such that its minimum angle θmin of cross-section is less than 120°, and more preferably 30° or more and less than 120°. Referring to FIGS. 9A and 9B, when an optional cross-section of the indenter 16 passing through the tip 16a so as to be vertical to the upper surface 10a of the chemically strengthened glass 10 (in the present embodiment, also vertical to the bottom surface 16b of the indenter 16) is taken as A, the angle θ of cross-section of the tip 16a means an angle at the tip 16a of a cross-section A. Furthermore, the minimum angle θmin of cross-section of the tip 16a means the smallest angle in the angle θ of cross-section at the tip 16a of a plurality of cross-sections A. For example, the minimum angle θmin of cross-section of the tip 16a of the indenter 16 in FIGS. 9A and 9B is an angle θ of cross-section of the tip 16a in a cross-section A' which passes through the respective middle points of two facing sides of the bottom surface 16b as well as the tip 16a, and is also vertical to the upper surface 10a of the chemically strengthened glass 10.

Thus, the indenter 16 arranged to face the upper surface 10a of the chemically strengthened glass 10 is pushed into the front surface of the chemically strengthened glass 10 under a static load condition. The static load condition means that a load is applied to the upper surface 10a of the chemically strengthened glass 10 to push the indenter 16 thereinto at a rate of 1 to 200 μm/sec, and the state is held for 1 second or more in the state that the load reached a preset load (0.01 kgf or more). The preset load is generally 200 kgf or less, and typically 50 kgf or less. As conventionally known, 1 kgf is 9.8N.

Figure 10A:
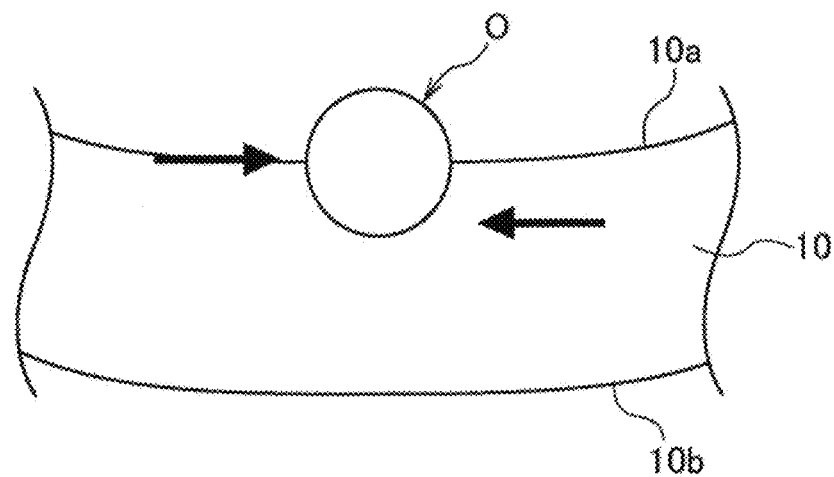
Figure 10B:
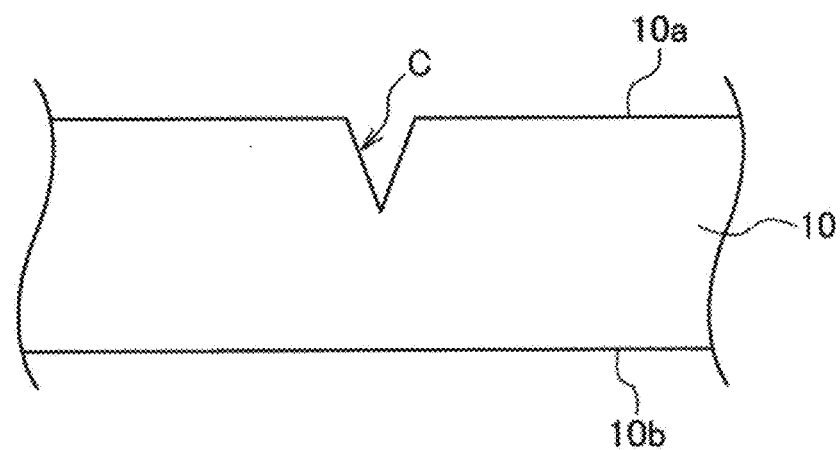

Thus, in the chemically strengthened glass 10 in which the indenter 16 was pushed and a flaw deeper than the depth of the compressive stress layer was formed, the fracture origin O occurs at a place deeper than the depth of the compressive stress force on the upper surface 10a. In this case, a compressive stress acts to the fracture origin O and a tensile stress acts to the circumference thereof (FIG. 10A). Subsequently, a tensile stress acts to the fracture origin O, crack C extends and a cover glass cracks (FIG. 10B). That is, although the difference exists in that the surface of the fracture origin is the upper surface or the lower surface, cracking occurs in the same mechanism as the slow cracking explained in FIGS. 2A and 2B.

In a case that a load of 3 kgf is applied to the chemically strengthened glass 10 (Glass A described hereinafter) by the indenter 16 having the minimum angle θmin of cross-section of the tip 16a of 110° as shown in FIG. 11, it is seen that one crack extends from the fracture origin and a cover glass is split in two, similar to FIG. 3B, and a cracking occurs in the same mechanism as in the slow cracking.

Thus, the chemically strengthened glass 10 in which the indenter 16 has been pushed is observed, and whether or not crack occurs, whether or not the glass cracks, and the like are evaluated by changing the minimum angle θmin of cross-section of the tip 16a of the indenter 16, the load by the indenter 16, the kind of the chemically strengthened glass 10, and the like.

In the chemically strengthened glass 10 according to the present invention, a depth of the compressive stress layer when a chemical strengthening has been conducted by dipping the glass in a potassium nitrate ($KNO_3$) molten salt at 435° C. for 4 hours is preferably 15 μm or more, and more preferably 30 μm or more. The compressive stress of the chemically strengthened glass is preferably 600 MPa or more, and more preferably 700 MPa or more.

The chemically strengthened glass 10 has a thickness of 1.5 mm or less, and more preferably from 0.3 to 1.1 mm. For example, a glass having the following composition is used.

(i) A glass containing from 50 to 80% of $SiO_2$, from 2 to 25% of $Al_2O_3$, from 0 to 10% of $Li_2O$, from 0 to 18% of $Na_2O$, from 0 to 10% of $K_2O$, from 0 to 15% of MgO, from 0 to 5% of CaO and from 0 to 5% of $ZrO_2$, as a composition in terms of mol %.

(ii) A glass containing from 50 to 74% of $SiO_2$, from 1 to 10% of $Al_2O_3$, from 6 to 14% of $Na_2O$, from 3 to 11% of $K_2O$, from 2 to 15% of MgO, from 0 to 6% of CaO and from 0 to 5% of $ZrO_2$, as a composition in terms of mol %, in which the total content of $SiO_2$ and $Al_2O_3$ is 75% or less, the total content of $Na_2O$ and $K_2O$ is from 12 to 25%, and the total content of MgO and CaO is from 7 to 15%.

(iii) A glass containing from 68 to 80% of $SiO_2$, from 4 to 10% of $Al_2O_3$, from 5 to 15% of $Na_2O$, from 0 to 1% of $K_2O$, from 4 to 15% of MgO and from 0 to 1% of $ZrO_2$, as a composition in terms of mol %.

(iv) A glass containing from 67 to 75% of $SiO_2$, from 0 to 4% of $Al_2O_3$, from 7 to 15% of $Na_2O$, from 1 to 9% of $K_2O$, from 6 to 14% of MgO and from 0 to 1.5% of $ZrO_2$, as a composition in terms of mol %, in which the total content of $SiO_2$ and $Al_2O_3$ is from 71 to 75%, the total content of $Na_2O$ and $K_2O$ is from 12 to 20%, and in the case of containing CaO, the content is less than 1%.

Examples of the present invention are described below.

Example 1

Chemically strengthened glass produced by a float process was cut into a size of 50 mm×50 mm, and ground to a removal of 300 μm or more using a grindstone of #1000 to form a plate-shaped glass having a thickness of 1 mm. The surface of the glass was polished using cerium oxide to form a mirror surface. The glass was chemically strengthened by dipping the glass in a potassium nitrate ($KNO_3$) molten salt at 425° C. for 10 hours. Surface compressive stress after chemical strengthening was about 700 MPa, and a depth of a compressive stress layer was about 45 μm.

The chemically strengthened glass 10 (hereinafter referred to as "Glass A") contained 72.5% of $SiO_2$, 6.2% of $Al_2O_3$, 12.8% of $Na_2O$ and 8.5% of MgO, as a composition in terms of mol %.

Strength of the chemically strengthened glass 10 was measured by the method of the above embodiment. Specifically, strength was measured by pushing the indenter 16 into the glass under a static load condition such that the tip 16a of the indenter 16 was vertical to the upper surface 10a of the chemically strengthened glass 10.

As the Vickers hardness tester 11 to which the indenter 16 was to be attached, FLS-ARS9000 manufactured by Future-Tech Corp was used. As the indenter 16, indenters having the minimum angle θmin of cross-section of the tip 16a of 136° (Comparative Example: Vickers indenter), 110° and 60°, respectively, were used. The indenter 16 was pushed into the upper surface 10a of the chemically strengthened glass 10 in a rate of 60 μm/sec until a load of from 0.05 to 3 kgf was applied to the indenter, and the state was held for 15 seconds in a state of having reached that load. The load to the indenter 16 was removed, and 60 seconds after, the cover glass was observed and evaluated.

As shown in FIG. 11, in the case of using the Vickers indenter in which the minimum angle θmin of cross-section of the tip 16a was 136°, indentation merely remained on the cover glass in any load, and a slow cracking could not be reproduced. Although not shown in FIG. 11, when the indenter was pushed until a load of 40 kgf was applied, a spider cracking could be observed. On the other hand, in the case of using the indenter 16 of the present invention in which the minimum angle θmin of cross-section of the tip 16a was 110°, a crack began to occur on the cover glass surface when the load reached 0.5 kgf, and a slow cracking could be observed when the load reached 3 kgf. Furthermore, in the case of using the indenter 16 in which the minimum angle θmin of cross-section of the tip 16a was 60°, a crack began to occur on the cover glass surface when the load reached 0.05 kgf, and a slow cracking could be observed when the load reached 0.5 kgf.

Thus, in the case that the indenter 16 of the present invention was used, it was confirmed that slow cracking can be reproduced, and even if a flat panel display device itself was not actually dropped, a slow cracking could be generated by using the chemically strengthened glass 10 alone. Consequently, the method of the present invention can be utilized in, for example, development of a new glass material that is resistant to slow cracking. Furthermore, since the indenter 16 is pushed into the upper surface 10a of the chemically strengthened glass 10 under a static load condition and the test can be conducted in the state that the shape of the indenter 16 has been controlled, reproducibility of the slow cracking can be improved as compared with the case of actually dropping a flat panel display device on the ground or the like.

Additionally, it is seen that the load at which crack or slow cracking occurs becomes smaller as the minimum angle θmin of cross-section of the tip 16a of the indenter 16 is smaller. It is considered that this is based on the following reason.

Figure 12A:
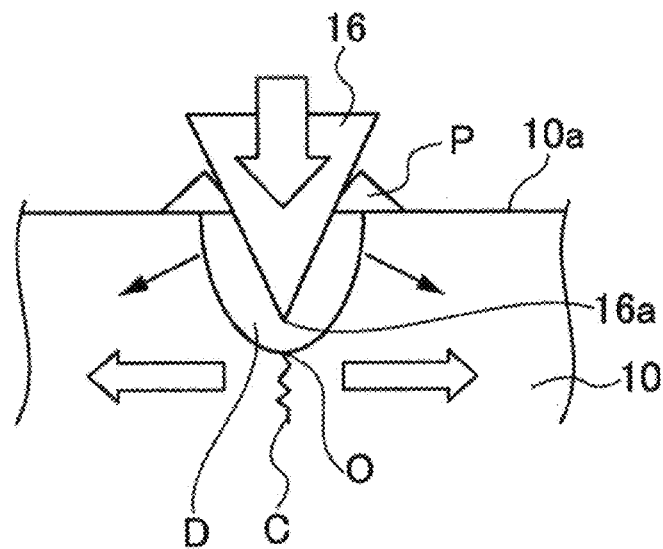
FIG. 12A is a view for explaining the state of a chemically strengthened glass into which an indenter having a small minimum angle of cross-section was pushed.

As shown in FIG. 12A, in the chemically strengthened glass 10 in which the indenter 16 is pushed, a densification region D at which the structure changes by the load of the indenter 16 to increase density is formed in a lower part of the indenter 16, and a plastic flow region P at which a part of the chemically strengthened glass 10 flows is formed in the periphery of the indenter 16. Incidentally, since the indenter 16 of the present invention is made to have a minimum angle θmin of cross-section of less than 120°, the load applied to the chemically strengthened glass 10 becomes such that a component force in a width direction is increased. Therefore, the densification region D is narrowed and the plastic flow region P is broadened, and additionally, large tensile stress acts to the fracture origin O near the tip 16a of the indenter 16, crack C extends and the cover glass tends to crack.

Figure 12B:
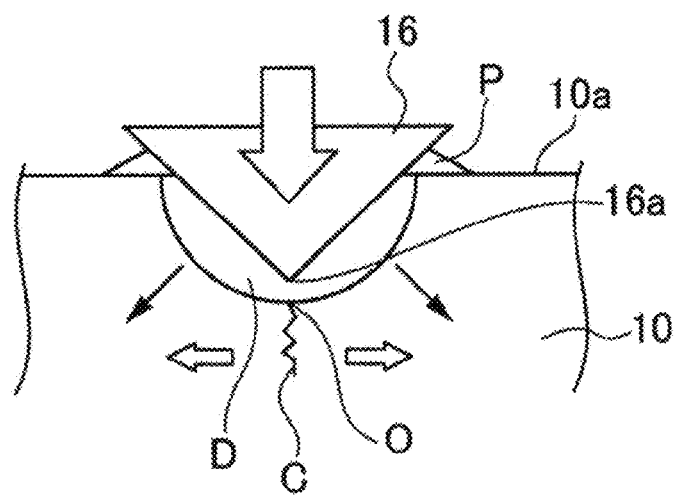
FIG. 12B is a view for explaining the state of a chemically strengthened glass into which an indenter having a large minimum angle of cross-section was pushed.

In contrast, as shown in FIG. 12B, in the case of using the indenter 16 having the minimum angle θmin of cross-section of 120° or more, typically in the case of using Vickers indenter, the load applied to the chemically strengthened glass 10 becomes such that a component force in a vertical direction is increased and a component force in a width direction is decreased. On the other hand, a pushing force in a vertical direction becomes strong, so that the densification region D broadens out in the glass pushed around the indenter 16. The densification region D receives tensile stress from the glass around the region that was not densified, and cracks may occur from the inside of the densification region D. However, many of such cracks extend in a horizontal direction, and therefore are difficult to contribute to fracture of a glass. Furthermore, the plastic flow region P becomes smaller as the angle of the intender 16 is increased. However, pushing force is relaxed by the occurrence of plastic flow, and as a result, crack C is difficult to occur.

Thus, in view of the points that easiness of fracture of the cover glass differs depending on the minimum angle θmin of cross-section of the tip 16a of the indenter 16, particularly fracture occurs with a lower load as the minimum angle θmin of cross-section is decreased, there is a possibility that the cover glass that has hitherto been considered to have sufficient crack resistance performance as a result of strength measurement using an indenter having a large minimum angle θmin of cross-section, such as Vickers indenter or knoop indenter, does not have sufficient slow cracking resistance performance when dropped on asphalt/concrete including sand and the like having small minimum angle θmin of cross-section (see FIGS. 7A and 7B).

Example 2

Based on the above findings, the present inventors have conducted strength measurement using the chemically strengthened glasses A to D having various properties in the same manner as in Example 1, and measured fracture probability. Glasses A to D have the following compositions.

Glass A: 72.5% of $SiO_2$, 6.2% of $Al_2O_3$, 12.8% of $Na_2O$ and 8.5% of MgO, as a composition in terms of mol %.

Glass B: 64.8% of $SiO_2$, 14.3% of $Al_2O_3$, 7.0% of $B_2O_3$, 13.4% of $Na_2O$ and 0.5% of $K_2O$, as a composition in terms of mol %.

Glass C: 68.2% of $SiO_2$, 8.8% of $Al_2O_3$, 14.2% of $Na_2O$, 1.3% of $K_2O$, 7.0% of MgO and 0.5% of CaO, as a composition in terms of mol %.

Glass D: 64.5% of $SiO_2$, 6.0% of $Al_2O_3$, 12.0% of $Na_2O$, 4.0% of $K_2O$ and 11.0% of MgO, as a composition in terms of mol %.

Glass A in this Example is a chemically strengthened glass similar to Glass A in Example 1 (see FIG. 11).

Table 1 shows probability (survival rate) of the chemically strengthened glasses A to D that were not division-fractured by indentation, and shows the probability in percent how many samples were not fractured in 10 samples under the same conditions. The survival rate is probability that glasses were not divided by that crack occurred by indentation reached a tensile stress layer and the crack freely run. In this Example, a load by the indenter 16 was changed in a range of from 0.2 to 50 kgf.

TABLE 1

| Minimum angle of cross-section | Glass | Load (kgf) | | | | | | | | | | | | | |
|---|---|---|---|---|---|---|---|---|---|---|---|---|---|---|---|
| | | 0.2 | 0.3 | 0.4 | 0.5 | 1 | 1.5 | 2 | 2.5 | 3 | 5 | 10 | 20 | 30 | 50 |
| 136° (Vickers indenter) | A | | | | | | | | | | | | 100% | 80% | 0% |
| | B | | | | | | | | | | | | | | 100% |
| | C | | | | | | | | | | | 100% | 10% | | |
| | D | | | | | | | | | | 70% | 0% | | | |
| 110° | A | | | | | | | 100% | 70% | 0% | | | | | |
| | B | | | | | | | 100% | 20% | 0% | | | | | |
| | C | | | | | | 100% | 70% | 20% | 0% | | | | | |
| | D | | | | | 100% | 20% | 10% | 0% | | | | | | |
| 60° | A | 100% | 100% | 100% | 20% | 0% | | | | | | | | | |
| | B | 100% | 40% | 0% | 0% | 0% | | | | | | | | | |
| | C | 100% | 100% | 20% | 0% | 0% | | | | | | | | | |
| | D | 100% | 100% | 100% | 80% | 0% | | | | | | | | | |

It is seen that any of Glasses A to D were destroyed by a lower load as the minimum angle θmin of cross-section of the tip 16a of the indenter 16 was decreased. This is the same as the reason as described in Example 1, and it is considered that, of the load applied to the chemically strengthened glass 10, a component force in a width direction becomes larger with the decrease of the minimum angle θmin of cross-section.

In the case of using Vickers indenter as same as conventionally used, concerning Glass A, 20% of the samples were fractured when the load of 30 kgf was applied, and 100% of the samples were fractured by the load of 50 kgf. Concerning Glass B, no sample was fractured even when any of the load was applied. Concerning Glass C, 90% of the samples were fractured by the load of 20 kgf. Concerning Glass D, 100% of the samples were fractured by the load of 10 kgf. Thus, in the case of using Vickers indenter, it is seen that the glasses were difficult to be fractured in the order of Glass B, Glass A, Glass C and Glass D.

In the case of using the indenter 16 having the minimum angle θmin of cross-section of 110°, the glasses were difficult to be fractured in the order of Glass A, Glass B, Glass C and Glass D. As compared with the case of using Vickers indenter, survival rates of Glasses A and B are reversed.

In the case of using the indenter 16 having the minimum angle θmin of cross-section of 60°, the glasses were difficult to be fractured in the order of Glass D, Glass A, Glass C and Glass B. Thus, Glass B that was most difficult to be fractured in the case of using Vickers indenter was most easily fractured. Glass D which was most easily fractured in the case of using Vickers indenter and in the case of using the indenter 16 having the minimum angle θmin of cross-section of 110° was most difficult to be fractured in the case of using the indenter having the minimum angle of cross-section of 60°.

The results are considered to be due to the reasons that Glass B has coarse structure as compared with other Glasses A, C and D, and has the characteristic that permits densification, and furthermore, Glass D has dense structure as compared with other Glasses A, B and C, and has high fracture toughness value, thus having the characteristic that cracking is difficult to occur.

It has been clarified from the above results that superiority or inferiority of the chemically strengthened glass 10 changes (is reversed) by the minimum angle θmin of cross-section of the tip 16a of the indenter 16, and slow cracking occurs by a lower load as the minimum angle θmin of cross-section is decreased. That is, it has been seen that there is a possibility that actual drop fracture of a flat display device is governed by the fracture by, for example, sand having small tip angle contained in asphalt/concrete. Therefore, when the minimum angle θmin of cross-section of the tip 16a of the indenter 16 falls within a range that a tip angle having high frequency is small (less than 120°, and preferably 30° or more and less than 120°; see FIG. 7B) among the tip angles of small stone, sand and the like contained in actual concrete/asphalt, as in the present invention, strength can be measured in the state close to the case of actual drop. As a result, the state of actual drop fracture can be reflected more appropriately.

As the method for producing a chemically strengthened glass, when the method for measuring strength as described above is employed in a production line, a threshold is determined by the above-described method for measuring strength while changing a load by an indenter, and a sampling inspection for judging quality of a chemically strengthened glass, particularly slow cracking resistance performance, is conducted on the basis of the threshold, cracking performance of a chemically strengthened glass can be controlled more accurately while further appropriately reflecting the state in the case that a flat panel display device has actually dropped. In the above Examples, the survival rate of the chemically strengthened glass is required to be a value optionally set or more, for example, 50% or more. In this case, the load at which the survival rate of the chemically strengthened glass becomes 50% is first determined as a threshold by the above-described method for measuring strength while changing the load by an indenter. In the actual production line, for example, 10 pieces of chemically strengthened glass among 1,000 pieces of chemically strengthened glass are sampled and inspected. In the case that 5 pieces or more chemically strengthened glass are not fractured as a result of applying a load corresponding the threshold, the quality of a chemically strengthened glass is guaranteed.

The present invention is not limited to the above-described embodiments in any way, and can be carried out in various embodiments in a scope that does not deviate from its gist.

For example, the shape of the indenter used in the present invention is not always limited to a right pyramid shape, and optional shape can be applied so long as the shape is a sharp shape such as a conical shape, an elliptic cone shape or a polyangular cone shape.

This application is based on Japanese patent application No. 2011-199555 filed Sep. 13, 2011, the entire contents thereof being hereby incorporated by reference.

What is claimed is:

1. A method for measuring strength of a chemically strengthened glass, comprising:
    applying a load to an indenter having a tip formed into a sharp shape having a minimum angle of cross-section of less than 120°;

pushing the indenter into a chemically strengthened glass having a compressive stress layer formed on a surface thereof under a static load condition such that the tip is vertical to the surface of the chemically strengthened glass; and measuring a strength of the chemically strengthened glass based on the load by which the chemically strengthened glass is fractured into parts.

2. The method according to claim 1, wherein the minimum angle of cross-section of the tip is 30° or more.

3. A method for producing a chemically strengthened glass, comprising:
   determining a threshold load for a chemically strengthened glass based on a strength measured by the method according to claim 1; and
   conducting a sampling inspection for judging quality of the chemically strengthened glass on a basis of the threshold load.

4. The method according to claim 3, wherein the minimum angle of cross-section of the tip is 30° or more.

5. The method according to claim 1, wherein a load by which the chemically strengthened glass is fractured into parts in a predetermined probability is determined as the strength of the chemically strengthened glass.

6. The method according to claim 1, wherein the chemically strengthened glass is fractured by a crack which has a fracture origin outside the compressive stress layer.

7. The method according to claim 1, wherein the static load condition is a condition in which the indenter is pushed at a rate of 1 to 200 µm/sec, and in which the indenter is held for 1 second or more.

8. The method according to claim 3, wherein the sampling inspection is conducted by an indentation with the threshold load using the indenter.

9. The method according to claim 3, wherein a load by which the chemically strengthened glass is fractured into parts in a predetermined probability is determined as the threshold load.

10. The method according to claim 9, wherein the sampling inspection is conducted by pushing the indenter into the chemically strengthened glass with the threshold load under the static load condition such that the tip of the indenter is vertical to the surface of the chemically strengthened glass, and by determining that the quality of the chemically strengthened glass is acceptable if a probability of fracture of a sample of the chemically strengthened glass is not more than the predetermined probability.

11. A method for measuring strength of a chemically strengthened glass, the method comprising:
    conducting a series of indentations on a chemically strengthened glass with changing loads applied in the series of indentations, the chemically strengthened glass having a compressive stress layer formed on a surface thereof, each indentation included in the series of indentations being conducted by applying the load to an indenter to be pushed into the chemically strengthened glass under a static load condition such that a tip of the indenter is vertical to the surface of the chemically strengthened glass, the tip of the indenter having a sharp shape which has a minimum angle of cross-section of less than 120°; and
    determining the load by which the chemically strengthened glass is fractured into parts in a predetermined probability, as a strength of the chemically strengthened glass.

12. The method according to claim 11, wherein the minimum angle of cross-section of the tip is 30° or more.

13. The method according to claim 11, wherein the chemically strengthened glass is broken by a crack which has a fracture origin outside the compressive stress layer.

14. The method according to claim 11, wherein the static load condition is a condition in which the indenter is pushed at a rate of 1 to 200 µm/sec, and in which the indenter is held for 1 second or more.

15. A method for producing a chemically strengthened glass, the method comprising:
    determining a threshold load for a chemically strengthened glass based on a strength measured by the method according to claim 11; and
    conducting a sampling inspection for judging quality of the chemically strengthened glass by an indentation with the threshold load using the indenter.

16. The method according to claim 15, wherein a load by which the chemically strengthened glass is fractured into parts in the predetermined probability is determined as the threshold load.

17. The method according to claim 16, wherein the sampling inspection is conducted by pushing the indenter into the chemically strengthened glass with the threshold load under the static load condition such that the tip of the indenter is vertical to the surface of the chemically strengthened glass, and by determining that the quality of the chemically strengthened glass is acceptable if a probability of fracture of a sample of the chemically strengthened glass is not more than the predetermined probability.

* * * * *